(12) United States Patent
O'Lenick, Jr. et al.

(10) Patent No.: US 7,247,696 B1
(45) Date of Patent: Jul. 24, 2007

(54) ALKYL DIMETHICONE COPOLYOL SULFOSUCCINATES

(76) Inventors: Anthony J. O'Lenick, Jr., 2170 Luke Edwards Rd., Dacula, GA (US) 30019; Kevin A. O'Lenick, 214 Elmbrook Dr., Canton, GA (US) 30047

( * ) Notice: Subject to any disclaimer, the term of this patent is extended or adjusted under 35 U.S.C. 154(b) by 311 days.

(21) Appl. No.: 11/112,913

(22) Filed: Apr. 25, 2005

Related U.S. Application Data

(60) Provisional application No. 60/655,265, filed on Feb. 22, 2005.

(51) Int. Cl.
   *C08G 77/22* (2006.01)

(52) U.S. Cl. .................... 528/30; 556/428; 528/26; 528/29; 528/33; 528/40

(58) Field of Classification Search ............... 528/29, 528/40; 556/400, 427, 450
   See application file for complete search history.

(56) References Cited

U.S. PATENT DOCUMENTS

| | | | | |
|---|---|---|---|---|
| 4,717,498 A | * | 1/1988 | Maxon | 556/428 |
| 4,849,127 A | * | 7/1989 | Maxon | 510/537 |

* cited by examiner

*Primary Examiner*—Cecilia J. Tsang
*Assistant Examiner*—Yate K Cutliff

(57) ABSTRACT

The present invention relates to dimethicone copolyol sulfosuccinates that contain alkyl groups having between 8 and 40 carbon atoms. More specifically, the invention relates to silicone-based sulfosuccinates that exhibit increased detergency while still maintaining mildness and foaming properties when used as surfactants in shampoos and other personal care products.

16 Claims, No Drawings

ALKYL DIMETHICONE COPOLYOL SULFOSUCCINATES

This application claims priority to and benefit of U.S. Provisional Application Nos. 60/655,265, filed Feb. 22, 2005, the disclosures of each of which are incorporated herein for all purposes.

FIELD OF THE INVENTION

The present invention relates to dimethicone copolyol sulfosuccinates that contain alkyl groups having between 8 and 40 carbon atoms. More specifically, the invention relates to silicone-based sulfosuccinates that exhibit increased detergency while still maintaining mildness and foaming properties when used as surfactants in shampoos and other personal care products.

BACKGROUND OF THE INVENTION

Sulfosuccinate surfactants have been used in the cosmetic industry primarily to improve the mildness of shampoos and other personal care products. Such surfactants are usually diesters or monoesters, with the monoester being preferred because of its mildness and foam enhancement properties. Heretofore, primarily two half ester or monoester derivatives have been used for shampoos which include derivatives of monoalcohol amides, such as oleamide MEA, oleamide IPA and undecylenamide MEA, and derivatives of fatty alcohols and ethoxylated alcohols, such as lauryl, laureth and oleyl alcohols.

The sulfosuccinates obtained from diesters and monoesters vary considerably in their foaming, viscosity building, solubility and conditioning properties. In general, they are gentle to the skin and eyes when compared to high foaming surfactants, and are usually blended with such high foaming surfactants to obtain surfactants which exhibit some degree of both mildness and foaming properties.

U.S. Pat. No. 4,849,127 issued Jul. 18, 1989 to Maxon incorporated herein by reference teaches Dimethicone copolyol sulfosuccinate compounds obtained from silicone-based monoesters. The dimethicone copolyol sulfosuccinates are obtained by reacting the ethoxylated polyether side chains of dimethicone copolyol with maleic anhydride to form a monoester and then converting the monoester to a sulfosuccinate by sulfonation of the double bond with a metallic sulfite, an amine or with a combination of a metallic sulfite and an amine. Dimethicone copolyol sulfosuccinates are silicone-based compounds which are useful as surfactants for improving the mildness and foam enhancing and stabilizing properties of shampoos and other personal care products. The patent is a division of co-pending application Ser. No. 000,479, filed on Jan. 5, 1987, now U.S. Pat. No. 4,717,498.

While silicone sulfosuccinate surfactants having mildness and foaming properties useful in the industry have been known and used, the preparation of such surfactants having both detergency and mildness in a silicone containing product has not been accomplished. The present invention is directed generally to alkyl silicone sulfosuccinate surfactants derived from alkyl silicone-based esters which demonstrate improved mildness, foam enhancing and stabilizing properties over known surfactants.

SUMMARY OF THE INVENTION

The present invention relates to a series of silicone based sulfosuccinates that contain an alkyl group that provides outstanding detergency as well as mildness to the skin and eye. While not wanting to be bound to any one theory, it is generally thought the compounds of the present invention function as follows: Consider the Maxon compounds (U.S. Pat. No. 4,894,127). The presence of only the sulfocuccinate on the silicone backbone results in a product that has surface active activity. This is because the hydrophobe is silicone based and is referred to as siliphilic (silicone loving). The alkoxylate and the sulfosuccinate group result in a hydrophilic and anionic group respectively. At the surface the water loving portion orients itself into the water phase and the silicone provides outstanding feel on the skin. What is missing is an oil soluble group to provide detergency, emulsifying and oils on the substrate into a micelle. By providing such a molecule, an outstanding detergent that is exceptionally mild and providing a good skin feel is achieved. The Maxon product lacks the desired detergency.

OBJECTS OF THE INVENTION

It is, an object of the present invention therefore, to prepare novel alkyl dimethicone copolyol sulfosuccinates having silicone-based compositions having improved detergency properties while maintaining good skin feel and mildness to the eye and skin.

Further objects of this invention are to prepare novel alkyl dimethicone copolyol sulfosuccinates which can be used as surfactants in shampoo and other personal care products and to provide novel multi-functional surfactants which exhibit improved detergency while still providing mildness and foam stabilizing properties.

These and other objects of the present invention together with the advantages thereof will become apparent to those skilled in the art from the detailed disclosure of preferred embodiments of the present invention as set forth below.

DETAILED DESCRIPTION OF THE INVENTION

The present invention relates generally to alkyl dimethicone copolyol sulfosuccinates of the formula:

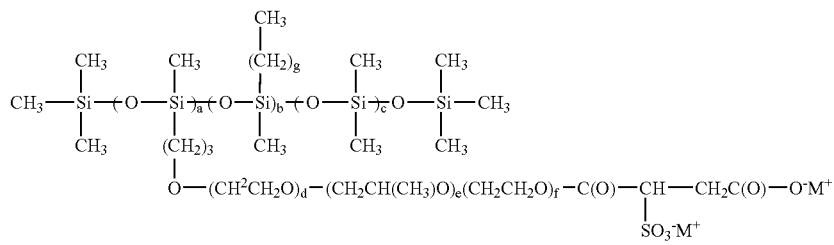

wherein;

a is an integer ranking from 1 to 20;

b is an integer ranging from 1 to 20;

c is an integer ranging from 0 to 200;

d, e and f are each independently integers ranging from 0 to 20;

g is an integer ranging from 7 to 39;

M is selected from the group consisting of sodium, potassium and ammonium.

The compositions of the present invention are generally prepared by reacting the ethoxylated polyether side chains of an alkyl dimethicone copolyol with maleic anhydride to form a monoester and then converting the monoester to a sulfosuccinate by sulfonation of the double bond with a metallic sulfite. Metallic sulfite and amine salts may also be used either alone or in combination for sulfonation of the double bond. The resulting sulfosuccinate is a silicone-based surfactant which exhibits highly improved mildness and foam stabilizing properties.

The alkyl dimethicone copolyol sulfosuccinate compositions of the present invention generally are prepared by reacting the ethoxylated polyether side chains of dimethicone copolyol with maleic anhydride to form a monoester. The side chains involved in this reaction are polymers or copolymers of ethylene or propylene oxide.

In the first step a preferred condensation reaction proceeds by reacting 1.00 moles of alkyl dimethicone copolyol with 1.0 to 1.30 moles of maleic anhydride. The dimethicone copolyol is heated to a temperature of 60°-100° C., with the preferred temperature ranging between 70°-90° C. The maleic anhydride is completely dissolved and dispersed and the reaction product, the maleic monoester of dimethicone copolyol, is then maintained at a temperature of 60°-100° C., preferably between 70°-90° C., under conditions and according to practices known to those skilled in the art until a constant acid value or number is obtained.

In the second step, the metallic sulfite is dissolved in water at a temperature of about 40° to 95° C., preferably between about 50° to 70° C. After the metallic sulfite is thoroughly dissolved, the maleic monoester of dimethicone copolyol is added to the solution, with the reaction product maintained in a fluid state. The product is allowed to react for approximately one half hour to three hours, until the concentration of the free metallic sulfite is between about 0 and 3%, with the preferred concentration less than about 2%.

PREFERRED EMBODIMENTS

In a preferred embodiment g is 7.
In a preferred embodiment g is 9.
In a preferred embodiment g is 11.
In a preferred embodiment g is 13
In a preferred embodiment g is 15.

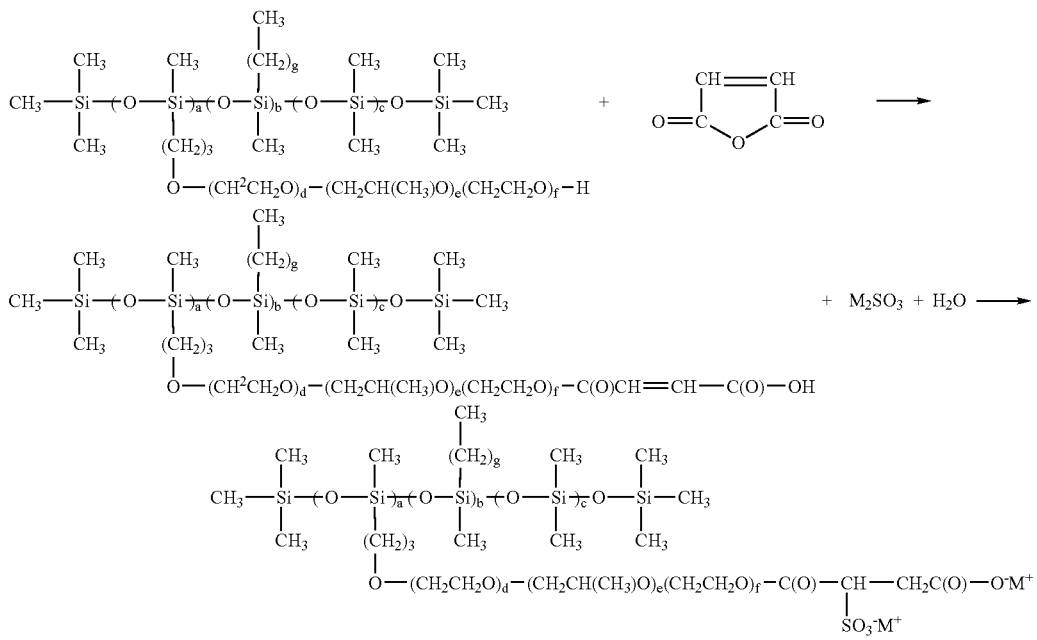

wherein;

a is an integer ranging from 1 to 20;

b is an integer ranging from 1 to 20;

c is an integer ranging from 0 to 200;

d, e and f are each independently integers ranging from 0 to 20;

g is an integer ranging from 7 to 39;

M is selected from the group consisting of sodium, potassium and ammonium.

In a preferred embodiment g is 17.
In a preferred embodiment g is 19.
In a preferred embodiment g is 21.
In a preferred embodiment g is 23
In a preferred embodiment g is 39.
In a preferred embodiment d+e+f is greater than 5.
In a preferred embodiment d+e+f is greater than 10.
In a preferred embodiment c is less than 100.
In a preferred embodiment c is less than 50.
In a preferred embodiment c is less than 20.

EXAMPLES

Alkyl Dimethicone Copolyols

The alkyl dimethicone copolyols useful as raw materials in the practice of the compounds of the present invention are available from Siltech LLC in Dacula Ga and conform to the following structure:

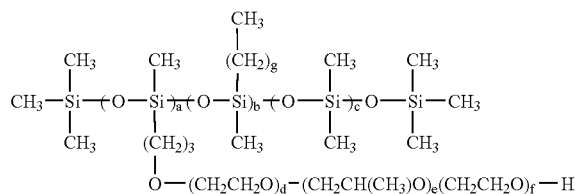

Examples 1-10

| Example | a | b | c | d | e | f | g |
|---|---|---|---|---|---|---|---|
| 1 | 1 | 1 | 0 | 8 | 5 | 5 | 7 |
| 2 | 5 | 1 | 5 | 0 | 0 | 0 | 11 |
| 3 | 10 | 5 | 10 | 3 | 5 | 6 | 9 |
| 4 | 4 | 5 | 15 | 10 | 0 | 0 | 13 |
| 5 | 15 | 10 | 5 | 0 | 10 | 0 | 15 |
| 6 | 17 | 20 | 1 | 0 | 5 | 10 | 17 |
| 7 | 15 | 1 | 200 | 20 | 20 | 20 | 19 |
| 8 | 20 | 3 | 5 | 8 | 8 | 8 | 21 |
| 9 | 6 | 1 | 1 | 0 | 20 | 20 | 39 |
| 10 | 2 | 1 | 0 | 5 | 5 | 5 | 23 |

Maleic Anhydride

Maleic anhydride is an item of commerce and conforms to the following structure:

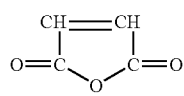

Metallic Sulfite Salts

Metallic sulfite salts are items of commerce and include:
Sodium sulfite ($Na_2SO_3$)
Potassium sulfite ($K_2SO_3$)
Ammonium sulfite ($(NH_4)_2SO_3$)

General Procedure

Maleamic Reaction

The reaction is carried out under anhydrous conditions with maleic anhydride and alkyl dimethicone copolyol. The reaction is generally carried out at 80-90° C., with a slight excess of maleic anhydride. A mole ratio of 1:1.05 is preferred.

To the specified number of grams of the specified alkyl dimethicone copolyol is added 103 grams of maleic anhydride under good agitation. The reaction mass is heated to 80° C. whereupon the maleic anhydride melts and begins to react. Care is taken to control the exotherm that ensues to keep the temperature below 95° C. The reaction mass is held for 8 hours and the reaction is complete when the acid value run in water is within 3 acid value units of the acid value run in anhydrous isopropanol.

| Alkyl Dimethicone Copolyol | | |
|---|---|---|
| Example | Example | Grams |
| 11 | 1 | 1174.0 |
| 12 | 2 | 242.6 |
| 13 | 3 | 370.6 |
| 14 | 4 | 846.3 |
| 15 | 5 | 383.3 |
| 16 | 6 | 552.3 |
| 17 | 7 | 1326.3 |
| 18 | 8 | 254.8 |
| 19 | 9 | 581.5 |
| 20 | 10 | 693.0 |

Sulfonation

The sulfonation reaction is carried out under aqueous conditions at a concentration of between 50% and 70% water by weight. The preferred amount of water is 65% by weight.

To the specified amount of water is added the specified number of grams of the specified metallic sulfite. The reaction mass is heated to 70° C. and the molten maleamic intermediated (Examples 11-20) is slowly added. Once the addition is complete the reaction mass is heated to 80-90° C. and held 3-5 hours. During that time the residual sulfite drops to very low levels as determined by titration with iodine.

| | Malemic Derivative | | Metallic Sulfite | | Water |
|---|---|---|---|---|---|
| Example | Example | Grams | Type | Grams | Grams |
| 21 | 11 | 1274.0 | Sodium Sulfite | 132.3 | 2611.7 |
| 22 | 12 | 342.6 | Sodium Sulfite | 132.3 | 882.0 |
| 23 | 13 | 470.6 | Ammonium Sulfite | 121.8 | 1100.2 |
| 24 | 14 | 946.3 | Ammonium Sulfite | 121.8 | 1983.6 |
| 25 | 15 | 483.3 | Potassium Sulifite | 168.0 | 1209.6 |
| 26 | 16 | 654.3 | Sodium Sulfite | 132.3 | 1460.8 |
| 27 | 17 | 1326.3 | Ammonium Sulfite | 121.8 | 2689.3 |
| 28 | 18 | 354.8 | Potassium Sulfite | 168.0 | 970.9 |
| 29 | 19 | 681.5 | Sodium Sulfite | 132.3 | 1511.3 |
| 30 | 20 | 793.0 | Potassium Sulfite | 168.0 | 1784.7 |

The compounds of the present invention are used as prepared without additional purification.

Applications Examples

Unlike the products made that lack the alkyl group, the compounds of the present invention are outstanding detergents and emulsifiers, not just foaming compositions. This makes them multi-functional and highly desirable in personal care applications.

The compounds of the present invention can be used as primary surfactants in baby shampoos, body washes and in bubble bath compositions, where very mild, sodium lauryl sulfate free products are desired. The use of these materials result in exceptionally mild detersive systems having outstanding mildness, wet comb and cleansing properties, while still supporting a no more tears claim.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. An alkyl dimethicone copolyol sulfosuccinate conforming to the following formula:

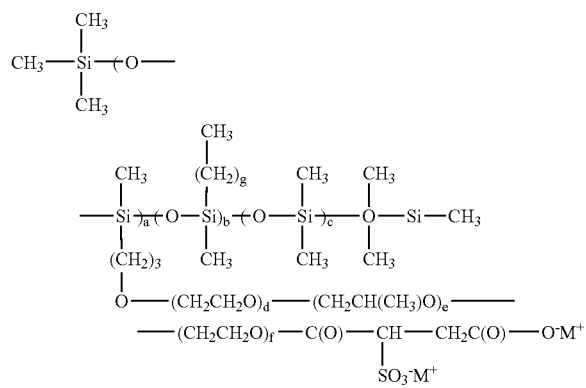

wherein;
- a is an integer ranking from 1 to 20;
- b is an integer ranging from 1 to 20;
- c is an integer ranging from 0 to 200;
- d, e and f are each independently integers ranging from 0 to 20;
- g is an integer ranging from 7 to 39;
- M is selected from the group consisting of sodium, potassium and ammonium.

2. An alkyl dimethicone copolyol sulfosuccinate of claim 1 wherein g is 7.

3. An alkyl dimethicone copolyol sulfosuccinate of claim 1 wherein g is 9.

4. An alkyl dimethicone copolyol sulfosuccinate of claim 1 wherein g is 11.

5. An alkyl dimethicone copolyol sulfosuccinate of claim 1 wherein g is 13.

6. An alkyl dimethicone copolyol sulfosuccinate of claim 1 wherein g is 15.

7. An alkyl dimethicone copolyol sulfosuccinate of claim 1 wherein g is 17.

8. An alkyl dimethicone copolyol sulfosuccinate of claim 1 wherein g is 19.

9. An alkyl dimethicone copolyol sulfosuccinate of claim 1 wherein g is 21.

10. An alkyl dimethicone copolyol sulfosuccinate of claim 1 wherein g is 23.

11. An alkyl dimethicone copolyol sulfosuccinate of claim 1 wherein g is 39.

12. An alkyl dimethicone copolyol sulfosuccinate of claim 1 wherein d+e+f is greater than 5.

13. An alkyl dimethicone copolyol sulfosuccinate of claim 1 wherein d+e+f is greater than 10.

14. An alkyl dimethicone copolyol sulfosuccinate of claim 1 wherein c is less than 100.

15. An alkyl dimethicone copolyol sulfosuccinate of claim 1 wherein c is less than 50.

16. An alkyl dimethicone copolyol sulfosuccinate of claim 1 wherein c is less than 20.

* * * * *